(12) United States Patent
Cowles et al.

(10) Patent No.: US 11,739,128 B2
(45) Date of Patent: Aug. 29, 2023

(54) PEPTIDE LIGASE-MEDIATED ENGINEERING OF RECOMBINANT NUCLEOSOMES

(71) Applicant: EPICYPHER, INC., Durham, NC (US)

(72) Inventors: Martis William Cowles, Chapel Hill, NC (US); Michael-Christopher Keogh, Cambridge, MA (US); Jonathan M. Burg, Durham, NC (US); Zu-Wen Sun, Brentwood, TN (US)

(73) Assignee: EPICYPHER, INC., Durham, NC (US)

(*) Notice: Subject to any disclaimer, the term of this patent is extended or adjusted under 35 U.S.C. 154(b) by 268 days.

(21) Appl. No.: 16/977,218

(22) PCT Filed: Mar. 7, 2019

(86) PCT No.: PCT/US2019/021106
§ 371 (c)(1),
(2) Date: Sep. 1, 2020

(87) PCT Pub. No.: WO2019/173565
PCT Pub. Date: Sep. 12, 2019

(65) Prior Publication Data
US 2021/0040164 A1 Feb. 11, 2021

Related U.S. Application Data

(60) Provisional application No. 62/639,802, filed on Mar. 7, 2018.

(51) Int. Cl.
C07K 14/47 (2006.01)
C12N 9/00 (2006.01)

(52) U.S. Cl.
CPC ............... *C07K 14/47* (2013.01); *C12N 9/93* (2013.01)

(58) Field of Classification Search
None
See application file for complete search history.

(56) References Cited

U.S. PATENT DOCUMENTS

2015/0152134 A1 6/2015 Pentelute et al.
2017/0122964 A1 5/2017 Schomburg et al.

FOREIGN PATENT DOCUMENTS

WO 2017/058114 4/2017

OTHER PUBLICATIONS

"Partial European Search Report corresponding to European Application No. 19763230.0 dated Dec. 3, 2021".
Nguyen, Giang K.T, et al., "Butelase-mediated cyclization and ligation of peptides and proteins", Nature Protocols 11(10):1977-1988 (Sep. 22, 2016).
Nguyen, Giang K.T, et al., "Site-Specific N-Terminai Labeling of Peptides and Proteins using Butelase 1 and Thiodepsipeptide", Angewandte Chemi International Edition 54(52):15694-15698 (Dec. 21, 2015).
Piotukh, Kirill , et al., "Directed Evolution of Sortase A Mutants with Altered Substrate Selectivity Profiles", J. Am. Chem. Soc. 133(44):17536-17539 (Nov. 9, 2011).
Schmidt, Marcel , et al., "Enzyme-mediated ligation technologies for peptides and proteins", Current Opinion in Chemical Biology 38:1-7 (Apr. 20, 2017).
International Preliminary Report on Patentability corresponding to International Application No. PCT/US2019/021106 dated Sep. 17, 2020.
"Extended European Search Report corresponding to European Application No. 19763230.0 dated Apr. 7, 2022".
Haridas, V , et al., "Sortase-Based Bio-organic Strategies far Macromolecular Synthesis", ChemBio Chem 15(13):1857-1867 (Aug. 8, 2014).
Leonen, Calvin Jon Antolin, et al., "Studies of biochemical crosstalk in chromatin with semisynthetic histones", Current Opinion in Chemical Bioiogy 45:27-34 (Feb. 27, 2018).
Li, Yi-Ming , et al., "Irreversible Site-Specific Hydrazinolysis of Proteins by Use of Sortase", Angew. Chem. Int. Ed. 53(8):2198-2202 (Feb. 17, 2014).
Müller, Manuel M, et al., "Histones: At the Crossroads of Peptide and Protein Chemistry", Chemical Reviews 115(6):2296-2349 (Mar. 25, 2015).
Popp, Maximilian Wei-Lin, et al., "Making and Breaking Peptide Bands: Protein Engineering Using Sortase". Angew. Chem. Int. Ed. 50(22):5024-5032 (May 23, 2011).
Schmohl, Lena , et al., "Engineering sortase A by screening a second-generation library using phage display", Journal of Peptide Science 23(7-8):631-635 (Feb. 10, 2017).
International Search Report and Written Opinion corresponding to International Application No. PCT/US2019/021106 dated Jun. 19, 2019.
Chatterjee, C. et al. "Chemical approaches for studying histone modifications", The Journal of Biological Chemistry 285(15):11045-11050 (2010).
Qi, Y. -K. et al. "Total Chemical Synthesis of Modified Histones", Frontiers in Chemistry vol. 6, Article No. 19, pp. 1-11 (2018).

*Primary Examiner* — Kagnew H Gebreyesus
(74) *Attorney, Agent, or Firm* — Myers Bigel, P.A.

(57) ABSTRACT

The invention relates generally to methods for preparing recombinant nucleosomes. In particular, the invention relates to methods for ligating a histone peptide onto a fully assembled recombinant nucleosome. The invention further relates to modified core histone proteins, histone peptides to be ligated to the modified core histone proteins, and fully assembled recombinant nucleosomes and libraries of recombinant nucleosomes prepared by the methods of the invention.

16 Claims, 4 Drawing Sheets

Specification includes a Sequence Listing.

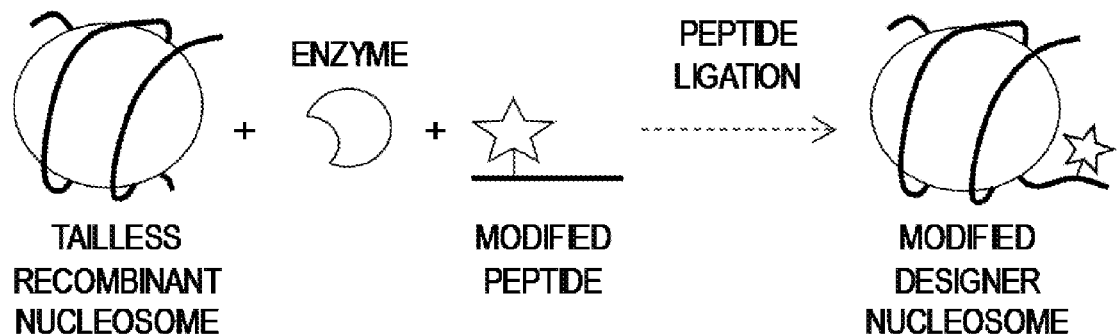
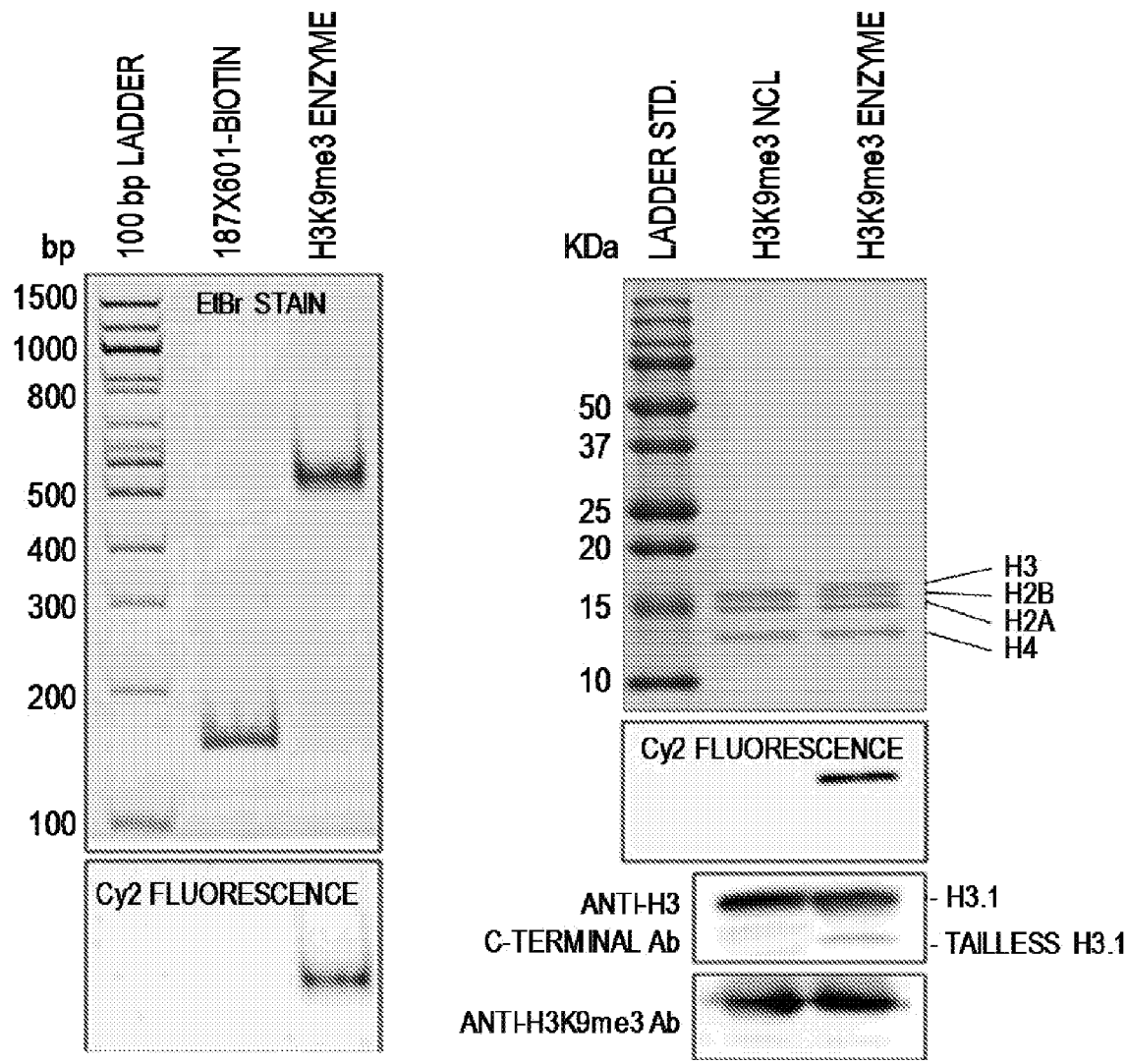
FIG. 1A
FIG. 1B
FIG. 1C

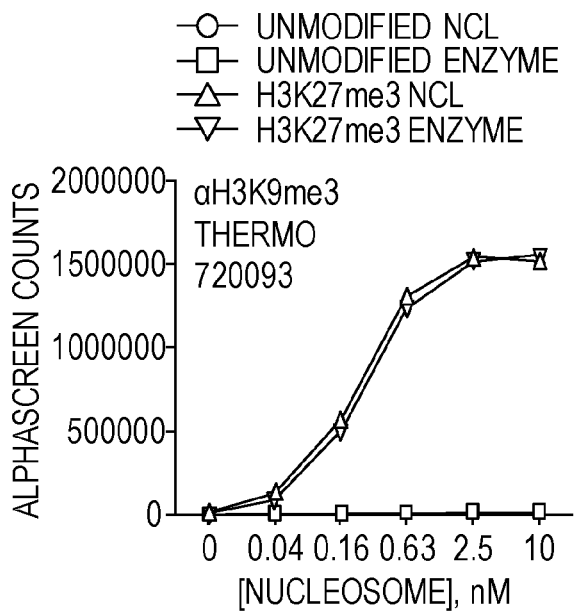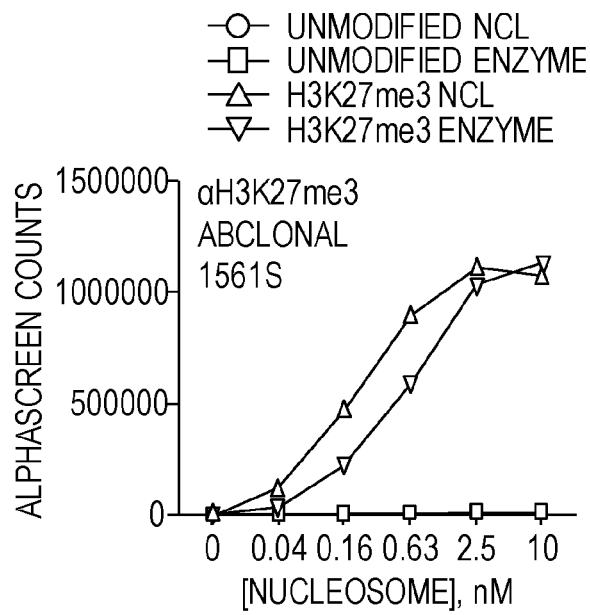
FIG. 3A
FIG. 3B
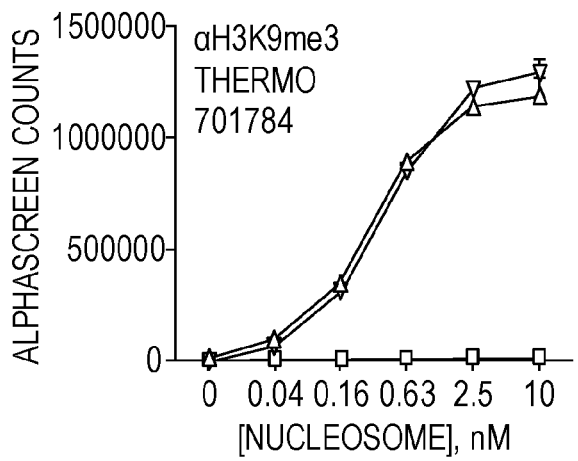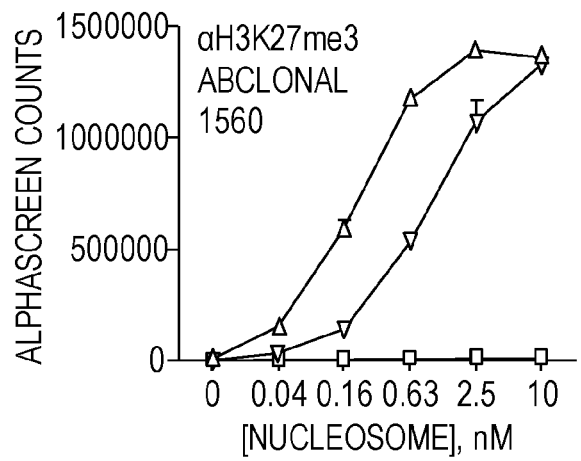
FIG. 3C
FIG. 3D
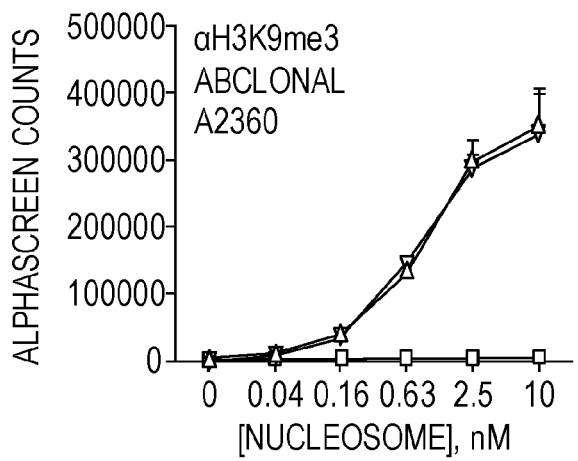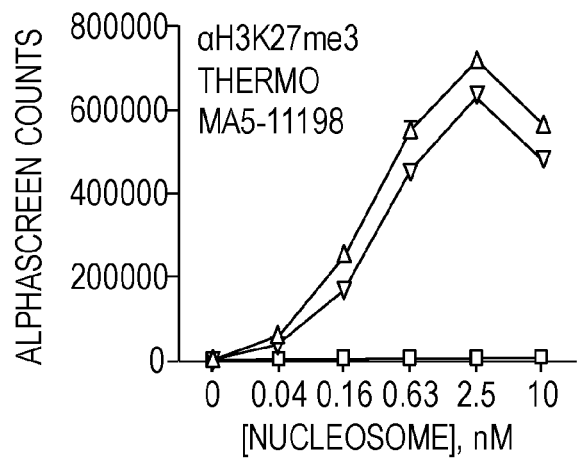
FIG. 3E
FIG. 3F

PEPTIDE LIGASE-MEDIATED ENGINEERING OF RECOMBINANT NUCLEOSOMES

STATEMENT OF PRIORITY

This application is a 35 U.S.C. § 371 national phase application of PCT Application PCT/US2019/021106, filed on Mar. 7, 2019, which claims the benefit of U.S. Provisional Application Ser. No. 62/639,802, filed on Mar. 7, 2018, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 1426-12_ST25.txt, 8,298 bytes in size, generated on Aug. 26, 2020 and filed via EFS-Web, is provided in lieu of a paper copy. This Sequence Listing is hereby incorporated by reference into the specification for its disclosures.

FIELD OF THE INVENTION

The invention relates generally to methods for preparing recombinant nucleosomes. In particular, the invention relates to methods for ligating a histone peptide onto a fully assembled recombinant nucleosome. The invention further relates to modified core histone proteins, histone peptides to be ligated to the modified core histone proteins, and fully assembled recombinant nucleosomes and libraries of recombinant nucleosomes prepared by the methods of the invention.

BACKGROUND OF THE INVENTION

Nucleosomes are the repeating units of chromatin and are comprised of a core histone octamer wrapped by ~147 bp DNA (Margueron et al., *Nat. Rev. Genet.* 11(4):285 (2010)). In addition to genome packaging, chromatin also regulates diverse cellular functions, including gene regulation, mitotic chromosome function, and DNA damage repair (Brown et al., *Hum. Mol. Genet.* 21(R1):R90 (2012); Lahtz et al., *J. Mol. Cell. Biol.* 3(1):51 (2011; Lunyak et al., *Hum. Mol. Genet.* 17(R1):R28 (2008); Reik, *Nature* 447(7143):425 (2007)). A key regulatory facet of these processes is mediated by histone post-translational modifications (PTMs), including methylation, acetylation, and phosphorylation. Over 100 unique histone PTMs (or combinations thereof) have thus far been linked to human disease, from neurodegeneration (Coppede, *Front. Genet.* 5:220 (2014)) to multiple cancers (Chopra et al., *Cancer Genet* 208(5):192 (2015); Greenblatt et al., *Leukemia* 28(7):1396 (2014); Gajer et al., *Oncogenesis* 4:e137 (2015); Witt et al., *Curr. Pharm. Des.* 15(4):436 (2009); Hanmod et al., *Pediatr. Blood Cancer* 62(1):52 (2015); Kobayashi et al., *Oncogene* 32(21): 2640 (2013)). Therefore, chromatin modifiers that add ('writers'), remove ('erasers'), or interpret ('readers') specific PTMs are compelling drug targets (Cai et al., *Mol. Cell* 60(4):561 (2015)). Moreover, histone PTMs are an emerging class of cancer biomarkers that may be useful for early disease detection and prognosis as well as informing personalized treatment strategies (Khan et al., *World J. Biol. Chem.* 6(4):333 (2015); Chervona et al., *Am. J. Cancer Res.* 2(5):589 (2012)).

Multivalency (i.e., multiple effector binding domains within a given protein) is a common feature of chromatin interacting proteins (Ruthenburg et al., *Nat. Rev. Mol. Cell. Biol.* 8(12):983 (2007)) and is thought to serve as a key mechanism by which the histone language is read/interpreted in a context-specific manner. Indeed, enzymatic activity and binding interactions of chromatin regulators are vastly altered in the presence of various PTMs or combinations thereof, a hypothesis known as the histone code (Cai et al., *Mol. Cell* 60(4):561 (2015); Khan et al., *World J. Biol. Chem.* 6(4):333 (2015)). For example, the bromodomain PHD finger transcription factor (BPTF) reader protein contains domains with low individual binding affinity for H3K4me3 ($K_d$=~1 µM) and H4K12ac ($K_d$=~60 µM) (Li et al., *Nature* 442(7098):91 (2006)), but this is significantly increased (>3-fold vs. H3K4me3 alone) in the presence of H3K4me3/H4K12ac combinatorially modified mononucleosomes (Ruthenburg et al., *Cell* 145(5):692 (2011)). BPTF is an anti-cancer therapy target (Dar et al., *J. Natl. Cancer Inst.* 107(5) (2015)); high levels are also found in amyotrophic lateral sclerosis patients (Mu et al., *Exp. Neurol.* 146(1):17 (1997)). Similarly, several chromatin-targeting enzymes have been shown to be stimulated or repressed via crosstalk with intranucleosomal histone and/or DNA modifications (Rothbart et al., *Biochim. Biophys. Acta* 1839(8): 627 (2014); Dann et al., *Nature* 548(7669):607 (2017); Zhang et al., *Cell Rep.* 12(9):1400 (2015); Rothbart et al., *Nat. Struct. Mol. Biol.* 19(11):1155 (2012); Harrison et al., *Elife* 5 (2016); Holt et al., *Proc. Natl. Acad. Sci. USA* 112(33):10365 (2015)). Recent findings have only begun to unravel the combinatorial impact of histone PTMs on cellular physiology and therefore disease.

Importantly, the presentation of these combinatorial histone PTMs depends on the 3-dimensional structure of the intact nucleosome, which serves as the physiological scaffold for these critical PTM-protein interactions. While some interactions between PTM marks on the same histone peptide (cis interactions) may be measurable by current peptide-based assay platforms (e.g., histone peptide arrays), the multivalent interactions (or 'crosstalk') between different histone subunits (trans interactions) require a nucleosome scaffold to be reproduced and measured (Khan et al., *World J. Biol. Chem.* 6(4):333 (2015); Li et al., *Nature* 442(7098): 91 (2006)). It is important to also note that several high value therapeutic targets make key interactions with non-PTM nucleosomal structures, such as DNA (unmodified/methylated) and unmodified histones (Rothbart et al., *Biochim. Biophys. Acta* 1839(8):627 (2014)); these interactions are essential to recapitulate in vivo activity (e.g., NSD2 (Pilotto et al., *Proc. Natl. Acad. Sci. USA* 112(9):2752 (2015)), LSD1 (Hsu et al., *ACS Chem. Biol.* 11(3):792 (2016)), and SIRT1 (Chen et al., *Chembiochem* 15(14):2071 (2014)). Despite this, the lack of existing tools means that most PTM interactions are currently studied in isolation using histone peptides, often with a single PTM.

Understanding the combinatorial nature of the histone code is vital to translating the connection(s) between epigenetic regulation and disease into next generation therapeutics and cancer biomarkers. Toward this goal, recombinant nucleosomes carrying specific histone modifications (termed designer nucleosomes or 'dNucs') are being developed. Unlike cell-derived nucleosomes (containing undefined, pre-existing pools of histone PTMs and DNA modifications), dNucs allow users to work with a homogeneous, fully-characterized nucleosome population. However, these reagents are technically challenging, costly, and time consuming to generate, thereby limiting their use in discovery applications.

The two leading technologies to seamlessly incorporate PTMs into histones are native chemical ligation (NCL) (Nguyen et al., *Chem. Biol.* 17(10):1072 (2010)) and Amber codon suppression (Nguyen et al., *J. Am. Chem. Soc.* 131 (40):14194 (2009); Neumann et al., *Mol. Cell* 36(1):153 (2009); Munari et al., *J. Biol. Chem.* 287(40):33756 (2012); Seeliger et al., *ACS Chem. Biol.* 7(1):150 (2012)). Although cysteine-based conjugation schemes (such as methyl-lysine analogs (MLA)) have also been explored, the incorporation of unnatural substrate mimics at the PTM site can dramatically alter interactions with enzymes, effector binding proteins, and antibodies (Nguyen et al., *Chem. Biol.* 17(10): 1072 (2010); Yanagisawa et al., *Chembiochem* 15(12):1830 (2014); Rogerson et al., *Nat. Chem. Biol.* 11(7):496 (2015); Pirman et al., *Nat. Commun.* 6:8130 (2015)). Amber suppression is useful for the rapid incorporation of PTMs (such as acetyl-lysine (Seeliger et al., *ACS Chem. Biol.* 7(1):150 (2012)) and phosphoserine (Heinemann et al., *FEBS Lett.* 586(20):3716 (2012)) into recombinant proteins, but is currently far less versatile than NCL. Indeed, Amber suppression can only efficiently incorporate a single modification type and is currently not amenable to several disease-relevant histone PTMs, including lysine trimethylation or arginine methylation. A major limitation of both NCL and Amber is that PTMs are added at the histone level, where these proteins must then be assembled into nucleosomes. Thus, each dNuc must be generated one-at-a-time using costly multistep methods, limiting manufacturing throughput. Given the remarkable PTM diversity found on chromatin in vivo, current methods cannot efficiently deliver the complexity required for next-generation target identification and biomarker discovery.

There is a need in the art for more versatile and efficient methods to produce designer nucleosomes.

SUMMARY OF THE INVENTION

This invention relates to the use of peptide ligases, e.g., butelase or transpeptidases, such as *S. aureus* Sortase A (sortase), in protein engineering for accelerated manufacturing of recombinant nucleosomes. This technology leverages a novel strategy where modified histone peptides are directly ligated onto fully assembled recombinant nucleosomes.

Thus, one aspect of the invention relates to a histone peptide that can be ligated to the N-terminus of a core histone protein, wherein the histone peptide comprises a C-terminal peptide ligase recognition site, e.g., a butelase or transpeptidase recognition site.

Another aspect of the invention relates to a modified core histone protein in which the N-terminal tail has been deleted and a sequence has been added to the N-terminus that is compatible with peptide ligation, e.g., an $X_1X_2$ sequence for butelase-mediated ligation, where $X_1$ is any amino acid except proline and $X_2$ is isoleucine, leucine, valine, or cysteine, or a GG sequence for transpeptidase-mediated ligation.

A further aspect of the invention relates to a polynucleotide encoding the modified core histone protein of the invention and vectors and host cells comprising the polynucleotide.

An additional aspect of the invention relates to a method for ligating a histone peptide onto a fully assembled recombinant nucleosome, the nucleosome comprising core histones and a polynucleotide wrapped around the core histones; the method comprising:

(a) contacting the histone peptide of the invention with a peptide ligase that recognizes the peptide ligase recognition site to produce a histone peptide-peptide ligase intermediate; and (b) contacting the histone peptide-peptide ligase intermediate with a fully assembled recombinant nucleosome comprising the modified core histone protein of the invention under conditions sufficient for ligation of the histone peptide to the modified core histone protein;

thereby producing a fully assembled recombinant nucleosome with a histone peptide ligated thereto.

Another aspect of the invention relates to a fully assembled recombinant nucleosome with a histone peptide ligated thereto, prepared by the method of the invention.

A further aspect of the invention relates to a library of recombinant nucleosomes, prepared by the method of the invention.

An additional aspect of the invention relates to a kit comprising the fully assembled recombinant nucleosome or the library of recombinant nucleosomes of the invention.

These and other aspects of the invention are set forth in more detail in the description of the invention below.

BRIEF DESCRIPTION OF THE DRAWINGS

FIGS. 1A-1C show enzyme-mediated peptide ligation for nucleosome manufacturing. (A) Schematic of the present enzymatic nucleosome production strategy, in which modified histone peptides are ligated to "tailless" nucleosome precursors. (B-C) Quality control metrics of H3K9me3-modified nucleosomes developed using enzyme mediated peptide ligation. Following ligation of a Cy2-labeled H3K9me3 peptide, native PAGE (B, top) and fluorescence imaging (B, bottom) was performed to confirm that DNA was stably associated with final histone octamer. No free DNA indicates that the nucleosome integrity is preserved throughout the ligation and purification workflow. Coomassie staining (C, top), was then performed showing that enzymatically-derived nucleosomes have equal stoichiometric ratios of histones H2A, H2B, 113, and H4, similar to NCL-developed nucleosomes. Fluorescence imaging (B, bottom; C, middle) and immunoblot for H3K9me3 (C, bottom panel) confirmed that H3K9me3 peptide was associated with final nucleosome product. Analysis of immunoblot for the unmodified C-terminus of H3 (C, bottom panel) revealed a ligation efficiency of ~85%.

FIGS. 3A-3F show enzymatically-derived nucleosomes are reliable substrates for profiling antibodies to specific histone post-translational modifications. Binding of anti-H3K9me3 and anti-H3K27me3 antibodies to NCL- and enzymatically-derived nucleosome substrates was compared using the AlphaScreen™ platform. All nucleosomes were assembled with biotinylated DNA, allowing their capture with streptavidin-coated Donor beads. Antibodies were detected using Protein A Acceptor beads, and antibody-nucleosome binding was quantified using the EnVision® plate reader. (A, C, E) Three different anti-H3K9me3 antibodies were tested against H3K9me3 nucleosomes. (B, D, F) Binding of three different anti-H3K27me3 antibodies against H3K27me3 nucleosomes was examined. In all experiments, unmodified recombinant nucleosomes (or those recreated by ligating an unmodified H3 peptide to "tailless" nucleosome precursor; i.e., Unmodified Enzyme) were included as negative controls.

DETAILED DESCRIPTION OF THE INVENTION

Figures 2A, 2B, 2C:
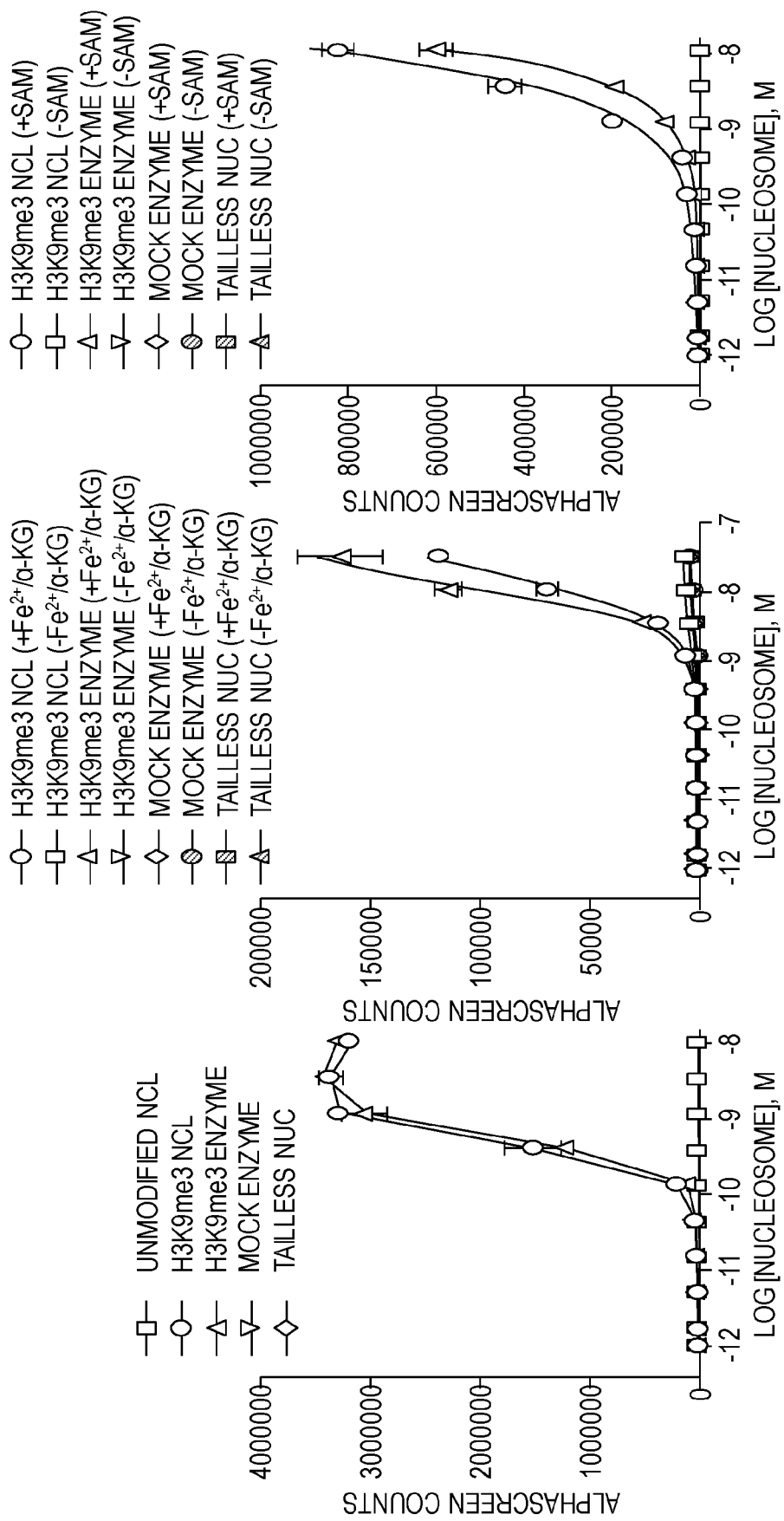
FIGS. 2A-2C show nucleosome substrates generated by enzyme-mediated ligation or NCL perform similarly in a variety of nucleosome binding and enzymatic assays. The AlphaScreen™ platform was used to compare the performance of enzymatic- and NCL-developed nucleosome substrates in chromatin binding and enzymatic assays. In all assays, nucleosomes were assembled with biotinylated DNA, allowing for their coupling to streptavidin-coated Donor beads. (A) The GST-tagged HP1β chromodomain was incubated with H3K9me3 nucleosomes. Interactions were quantified on the EnVision® plate reader, following addition of Donor beads and glutathione-coated Acceptor beads (binds HP1β). (B) H3K9me3 nucleosomes were incubated with the histone demethylase KDM4A, followed by detection on AlphaScreen™ using an antibody specific for H3K9me1. (C) Unmodified recombinant nucleosomes were used as substrates for the H3K9 methyltransferase G9a, and levels of H3K9me2 detected in AlphaScreen™. In (B-C), antibody-PTM binding was detected using Protein A Acceptor beads (binds antibody).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of nucleosomes, and transiently and stably transfected cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid, protein means that the nucleic acid or protein does not contain any element other than the recited element(s) that significantly alters (e.g., more than about 1%, 5% or 10%) the function of interest of the nucleic acid or protein.

With respect to polypeptide and polynucleotide sequences, the term "consisting essentially of" means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in a biological activity (e.g., nucleosome formation) of at least about 50% or more as compared to the activity of a polypeptide consisting of the recited sequence.

As used herein, the term "polypeptide" encompasses both peptides and proteins, unless indicated otherwise.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA (including both naturally occurring and non-naturally occurring nucleotides). The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By "substantially retain" a property, it is meant that at least about 75%, 85%, 90%, 95%, 97%, 98%, 99% or 100% of the property (e.g., activity or other measurable characteristic) is retained.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., at least 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention. In some embodiments, such fragments can comprise, consist essentially of, and/or consist of oligonucleotides having a length of less than about 8, 10, 12, 15, 20, 25, 30, 35, 40, 45, 50, 75, 100, 150, or 200 consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., at least 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. In some embodiments, such fragments can comprise, consist essentially of, and/or consist of peptides having a length of less than about 4, 6, 8, 10, 12, 15, 20, 25, 30, 35, 40, 45, 50, 75, 100, 150, or 200 consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., nucleosome formation). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as nucleosome formation can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

This invention relates based on the development of protein engineering methods for accelerated manufacturing of recombinant nucleosomes. This technology leverages a novel 'on-nucleosome' ligation strategy where modified histone peptides are directly ligated onto fully assembled recombinant nucleosomes. The methods provide the ability to efficiently introduce post-translational modifications (PTMs) into nucleosomes.

Thus, one aspect of the invention relates to a peptide to be ligated to a histone present in a nucleosome. The peptide mimics the N-terminal tail of the histone and may comprise one or more PTMs to be introduced to the nucleosome. In some embodiments, the invention relates to a histone peptide that can be ligated to the N-terminus of a core histone protein, wherein the histone peptide comprises a peptide ligase recognition site, e.g., a C-terminal butelase or transpeptidase recognition site. The sequence of the histone peptide corresponds to the N-terminal tail sequence of a core histone protein, e.g., H2A, H2B, H3, or H4. The N-terminal tail sequence of the core histones is well known and exemplary histone sequences are indicated in Table 1 with the N-terminal tails underlined. The length of the N-terminal tail varies for each histone: approximately 14-18 residues for H2A, 33-37 residues for H2B, 42-46 residues for H3, and 24-28 residues for H4. In some embodiments, the core histone protein is histone H3, e.g., a variant backbone of H3 such as H3.1, H3.2, or H3.3.

TABLE 1

| Histone | UniProt Accession No. | Sequence |
|---|---|---|
| H2A | P0C0S8 | MSGRGKQGGK ARAKAKTRSS RAGLQFPVGR VHRLLRKGNY AERVGAGAPV YLAAVLEYLT AEILELAGNA ARDNKKTRII PRHLQLAIRN DEELNKLLGK VTIAQGGVLP NIQAVLLPKK TESHHKAKGK (SEQ ID NO: 1) |
| H2B | P62807 | MPEPAKSAPA PKKGSKKAVT KAQKKDGKKR KRSRKESYSV YVYKVLKQVH PDTGISSKAM GIMNSFVNDI FERIAGEASR LAHYNKRSTI TSREIQTAVR LLLPGELAKH AVSEGTKAVT KYTSSK (SEQ ID NO: 2) |
| H3.1 | P68431 | MARTKQTARK STGGKAPRKQ LATKAARKSA PATGGVKKPH RYRPGTVALR EIRRYQKSTE LLIRKLPFQR LVREIAQDFK TDLRFQSSAV MALQEACEAY LVGLFEDTNL CAIHAKRVTI MPKDIQLARR IRGERA (SEQ ID NO: 3) |
| H3.2 | Q71DI3 | MARTKQTARK STGGKAPRKQ LATKAARKSA PATGGVKKPH RYRPGTVALR EIRRYQKSTE LLIRKLPFQR LVREIAQDFK TDLRFQSSAV MALQEASEAY LVGLFEDTNL CAIHAKRVTI MPKDIQLARR IRGERA (SEQ ID NO: 4) |
| H4 | P62805 | MSGRGKGGKG LGKGGAKRHR KVLRDNIQGI TKPAIRRLAR RGGVKRISGL IYEETRGVLK VFLENVIRDA VTYTEHAKRK TVTAMDVVYA LKRQGRTLYG FGG (SEQ ID NO: 5) |

The histone may comprise the same amino acid sequence as the N-terminal tail sequence or a similar sequence as the N-terminal tail sequence, e.g., at least about 70%, 80%, 90%, 91%, 92%, 93%, 94%, 95%, 96%, 97%, 98%, or 99% identical. The histone peptide may comprise a functional fragment of the N-terminal tail sequence, e.g., the N-terminal tail sequence in which one or more amino acids have been removed from the N-terminal and/or C-terminal end of the tail, e.g., a total of 1, 2, 3, 4, 5, 6, 7, 8, 9, 10, 11, 12, 13, 14, or 15 amino acids.

In some embodiments, the histone peptide comprises at least one PTM, e.g., 1, 2, 3, 4, or 5 or more PTMs. The at least one PTM may include, without limitation, lysine methylation, lysine acylation, serine phosphorylation, lysine ubiquitylation, arginine methylation, and any combination thereof.

The peptide ligase recognition site may be located anywhere in the C-terminal portion of the peptide. The C-terminal portion is defined as the residues in the C-terminal half of the peptide. In some embodiments, the recognition site is at the C-terminus. In some embodiments, the recognition site is near the C-terminus, e.g., within 10, 9, 8, 7, 6, 5, 4, or 3 residues of the C-terminus.

The peptide ligase recognition site may be any sequence recognized by a peptide ligase capable of ligating the histone peptide to a histone protein.

The butelase recognition site may be any sequence recognized by a butelase capable of ligating the histone peptide to a histone protein. The butelase-1 recognition site is the amino acid sequence (N/D)HV (US 2018/0274003 and Nguyen et al., *Nature Protocols* 11(10):1977 (2016), each incorporated herein by reference in its entirety). In some embodiments, the recognition site may contain an altered residues at the scissile bond (e.g., a thiodepsipeptide or depsipeptide, e.g., an (S)GV or (O)GV analog instead of HV) to inhibit the reverse ligation reaction with the cleaved dipeptide HV (Nguyen et al., *Angew. Chem. Int. Ed* 54:15694 (2015), incorporated by reference in its entirety).

The transpeptidase recognition site may be any sequence recognized by a transpeptidase capable of ligating the histone peptide to a histone protein. In some embodiments, the transpeptidase recognition site is a sortase recognition site.

Based on their amino acid sequences, there are at least six types of sortases (class A to F enzymes). Class A is the archetypal sortase from *S. aureus*: comprising a canonical cell wall sorting signal (CWS) consisting of an LPXTG (SEQ ID NO:6) motif. Class B sortases are known to recognize and cleave only the NPQTN (SEQ ID NO:7) sorting signal [NP(Q/K)(T/S)(N/G/S)(D/A)] (SEQ ID NO:8) (e.g., *S. aureus* and *B. anthracis* SrtB). Class C sortases function to assemble pili by joining SpaA,B,C subunits. They recognize the LPLTG (SEQ ID NO:9) sorting motif cleaving the T/G bond but creating an isopeptide bond between the acyl-enzyme intermediate and the lysine amine of "pilin' motif" (WXXXVXXYPK) (SEQ ID NO:10) (e.g., *S. pneumoniae* Cd-SrtA). Class D sortases are known to recognize closely related sorting signals to class A sortases, such as an LPNTA (SEQ ID NO:11) motif (e.g., BasH and BasI of *B. anthracis*). Class E sortases are used by soil and freshwater-dwelling Actinobacteria to display proteins that contain a non-canonical LAXTG (SEQ ID NO:12) sorting signal, which differs from 90% of known sorting signals by substitution of alanine for proline (e.g., SrtE1 *Streptomyces coelicolor*). Class F includes at least 57 sortases that have been identified in various Actinobacteria such as *Streptomyces coelicolor, Streptomyces avermitillis*, and *Thermobifida fusca*.

In some embodiments, the sortase recognition site is the amino acid sequence APXTG (SEQ ID NO:13), wherein X is any amino acid. In certain embodiments, X is A or S.

In some embodiments, the sortase recognition site is the amino acid sequence LPXTG (SEQ ID NO:6), wherein X is any amino acid. In certain embodiments, X is A or S. In certain embodiments, the sortase recognition site is the amino acid sequence LPATG (SEQ ID NO:14).

In some embodiments, the histone peptide may further comprise a tag on the C-terminal end of the histone peptide. The tag may be directly C-terminal of the peptide ligase recognition site or there may be one or more amino acid residues between the tag and the peptide ligase recognition site, e.g., 1, 2, 3, 4, or 5 or more residues. The tag may be any agent that is useful for identifying and/or isolating the histone peptides. In some embodiments, the tag is a label, e.g., a radioactive, luminescent, or fluorescent label. In some embodiments, the tag is an amino acid sequence or other moiety that is recognized by an agent that can be used to isolate the peptide, e.g., an epitope tag, e.g., a FLAG, His, Myc, GST, HA, or V5 tag. The tag may be removable, e.g., by cleavage, after the histone peptide has been isolated.

The histone peptides of the invention may be prepared by any method known in the art. In some embodiments, the histone peptides are synthesized by standard peptide synthesis techniques.

Another aspect of the invention relates to core histone protein that has been modified to accept ligation to the histone peptide of the invention. The modified histone has some or all of the N-terminal tail deleted and optionally has one or more amino acid residues added to create a sequence suitable for peptide ligase-catalyzed ligation of the histone peptide. In some embodiments, the invention relates to a modified core histone protein in which the N-terminal tail has been deleted and an $X_1X_2$ amino acid sequence added to the N-terminus to be suitable for butelase ligation, where $X_1$ is any amino acid except proline and $X_2$ is isoleucine, leucine, valine, or cysteine. In some embodiments, the invention relates to a modified core histone protein in which the N-terminal tail has been deleted and a GG amino acid sequence added to the N-terminus to be suitable for transpeptidase ligation. The core histone protein may be H2A, H2B, H3, or H4. In some embodiments, the core histone protein is histone H3, e.g., a variant backbone of H3 such as H3.1, H3.2, or H3.3. In some embodiments, the entire N-terminal tail is deleted. In some embodiments, a substantial portion of the N-terminal tail is deleted, e.g., 60%, 70%, 80%, 90%, 91%, 92%, 93%, 94%, 95%, 96%, 97%, 98%, or 99%.

The core histone proteins used as a starting point to design the modified histones of the invention may be from any species of interest. Histone sequences may be found in databases such as GenBank and UniProt. Exemplary human histone sequences are listed in Table 1, with the N-terminal tail underlined. In one embodiment, the core histones are human histones or fragments, variants, or homologs thereof. As used herein, the term "homolog" is used to refer to a polypeptide which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and substitutions), changes in stereochemistry of one or a few atoms, and minor derivatizations, including, without limitation, methylation, glycosylation, phosphorylation, acylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., nucleosome forming activity), e.g., about 30%, 40%, 50% or more.

In some embodiments, the modified histone protein comprises, consists essentially of, or consists of the wild-type sequence of the protein or a functional fragment thereof. In another embodiment, the modified histone protein comprises, consists essentially of, or consists of an amino acid sequence that is at least 70% identical, e.g., at least 75%, 80%, 85%, 90%, 95%, 96%, 97%, 98%, or 99% identical to the publicly known amino acid sequence or a functional fragment thereof.

The modified histone protein of the invention also include functional portions or fragments. The length of the fragment is not critical as long as it substantially retains the biological activity of the polypeptide (e.g., nucleosome forming activity). Illustrative fragments comprise at least about 4, 6, 8, 10, 12, 15, 20, 25, 30, 35, 40, 45, 50, 75, 100, 150, 200, or more contiguous amino acids of a histone protein.

Likewise, those skilled in the art will appreciate that the present invention also encompasses fusion polypeptides comprising the modified histone protein (or a functional fragment thereof). For example, it may be useful to express the modified histone protein (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein (MBP) or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the modified histone proteins specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 2

| Amino Acid | | | Codons | | | | | |
|---|---|---|---|---|---|---|---|---|
| Alanine | Ala | A | GCA | GCC | GCG | GCT | | |
| Cysteine | Cys | C | TGC | TGT | | | | |
| Aspartic acid | Asp | D | GAC | GAT | | | | |
| Glutamic acid | Glu | E | GAA | GAG | | | | |
| Phenylalanine | Phe | F | TTC | TTT | | | | |

TABLE 2-continued

| Amino Acid | | | Codons | | | | | |
|---|---|---|---|---|---|---|---|---|
| Glycine | Gly | G | GGA | GGC | GGG | GGT | | |
| Histidine | His | H | CAC | CAT | | | | |
| Isoleucine | Ile | I | ATA | ATC | ATT | | | |
| Lysine | Lys | K | AAA | AAG | | | | |
| Leucine | Leu | L | TTA | TTG | CTA | CTC | CTG | CTT |
| Methionine | Met | M | ATG | | | | | |
| Asparagine | Asn | N | AAC | AAT | | | | |
| Proline | Pro | P | CCA | CCC | CCG | CCT | | |
| Glutamine | Gln | Q | CAA | CAG | | | | |
| Arginine | Arg | R | AGA | AGG | CGA | CGC | CGG | CGT |
| Serine | Ser | S | AGC | ACT | TCA | TCC | TCG | TCT |
| Threonine | Thr | T | ACA | ACC | ACG | ACT | | |
| Valine | Val | V | GTA | GTC | GTG | GTT | | |
| Tryptophan | Trp | W | TGG | | | | | |
| Tyrosine | Tyr | Y | TAC | TAT | | | | |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

Another aspect of the invention relates to a polynucleotide encoding the modified core histone protein of the invention.

A further aspect of the invention relates to a vector comprising the polynucleotide of the invention.

An additional aspect of the invention relates to a cell comprising the polynucleotide or the vector of the invention.

In other embodiments, polynucleotide sequences encoding the modified histone have at least about 70%, 80%, 85%, 90%, 95%, 96%, 97%, 98%, 99% or higher sequence identity with the publicly known nucleic acid sequences (e.g., as disclosed in the GenBank) or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 2).

Likewise, the polypeptides (and fragments thereof) of the invention include polypeptides that have at least about 70%, 80%, 85%, 90%, 95%, 96%, 97%, 98%, 99% or higher amino acid sequence identity with the publicly known polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the modified histones of the invention will typically be associated with appropriate expression control sequences, e.g., transcription/translation control signals and polyadenylation signals.

The present invention further provides cells, e.g., bacteria, comprising the isolated polynucleotides and polypeptides of the invention.

The isolated polynucleotide can be incorporated into an expression vector. Expression vectors compatible with various host cells are well known in the art and contain suitable elements for transcription and translation of nucleic acids. Typically, an expression vector contains an "expression cassette," which may include, in the 5' to 3' direction, a promoter, a coding sequence encoding the modified histone or functional fragment thereof operatively associated with the promoter, and, optionally, a termination sequence including a stop signal for RNA polymerase and a polyadenylation signal for polyadenylase.

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Another aspect of the invention relates to methods for ligating a histone peptide of the invention onto a fully assembled nucleosome comprising the modified core histone protein of the invention. One aspect of the invention relates to a method for ligating a histone peptide onto a fully assembled recombinant nucleosome, the nucleosome comprising core histones and a polynucleotide wrapped around the core histones; the method comprising:
(a) contacting the histone peptide of the invention with a peptide ligase (e.g., butelase or transpeptidase) that recognizes the peptide ligase recognition site to produce a histone peptide-peptide ligase intermediate; and
(b) contacting the histone peptide-peptide ligase intermediate with a fully assembled recombinant nucleosome comprising the modified core histone protein of the invention under conditions sufficient for ligation of the histone peptide to the modified core histone protein;
thereby producing a fully assembled recombinant nucleosome with a histone peptide ligated thereto.

In some embodiments, the peptide ligase is a butelase (e.g., butelase 1 or OaAEP1b) or a transpeptidase (e.g., sortase A). Other known peptide ligases include, without limitation, PATG, PCY1, and POBP.

In some embodiments, the transpeptidase is a sortase family enzyme. The enzyme may be a wild-type sortase, e.g., *Staphylococcus aureus* sortase A. In other embodiments, the sortase may comprise one or more mutated residues that alter activity or specificity. Such modified sortase variants are known in the art and include, for example, the sortases disclosed in U.S. Pat. No. 9,267,127, incorporated by reference herein in its entirety.

The nucleosome(s) used in the methods of the invention may be any nucleosome of interest. In some embodiments, the fully assembled nucleosome comprises at least one PTM, e.g., at least about 1, 2, 3, 4, 5, or more PTMs. At least one PTM may be, without limitation, lysine methylation, lysine acylation, serine phosphorylation, lysine ubiquitylation, arginine methylation, and any combination thereof.

In some embodiments, the fully assembled nucleosome comprises at least one post-transcriptional modification on the polynucleotide sequence, e.g., at least about 1, 2, 3, 4, 5, or more post-transcriptional modifications. The at least one post-transcriptional modification may be, without limitation, 5-methylcytosine, 5-hydroxymethylcytosine, 5,6-dihydrouracil, 7-methylguanosine, xanthosine, inosine, and any combination thereof.

In some embodiments, the fully assembled nucleosome comprises at least one histone variant.

A further aspect of the invention relates to a fully assembled recombinant nucleosome with a histone peptide ligated thereto, prepared by the method of invention.

An additional aspect of the invention relates to a library of recombinant nucleosomes, prepared by the method of the invention. The library may contain nucleosomes having at least 2 different modification patterns, e.g., at least 4, 6, 8, 10, 12, 14, 16, 18, 20, 25, 30, 35, 40, 50, 100 or 150 or more different patterns. The library may contain some or all of the possible modifications of a particular type, e.g., lysine methylation, arginine methylation, or arginine acylation. The library may include some or all of the modifications considered to be relevant to one or more diseases. In some embodiments, the kit may comprise a library that represents most or all of the different possibilities of histone mutations, e.g., oncogenic histone mutations, e.g., of a single histone or multiple histones. The library may be used to assess the specificity of affinity reagents, monitor technical variability, and normalize experiments.

A further aspect of the invention relates to a kit useful for carrying out the methods of the invention. The kits may contain reagents for carrying out the methods. The reagents may be included in suitable packages or containers. In some embodiments, the kit may comprise the fully assembled recombinant nucleosome of the invention or the library of recombinant nucleosomes of the invention. The kit may further include one or more peptide ligases as described herein.

When a kit is supplied, the different components may be packaged in separate containers and admixed immediately before use. Such packaging of the components separately may permit long-term storage without losing the active components' functions. Kits may also be supplied with instructional materials. Instructions may be printed on paper or other substrate, and/or may be supplied as an electronic-readable medium.

Having described the present invention, the same will be explained in greater detail in the following examples, which are included herein for illustration purposes only, and which are not intended to be limiting to the invention.

EXAMPLES

Example 1: Enzyme-Mediated Peptide Ligation for Nucleosome Manufacturing

Current approaches to generate modified recombinant nucleosomes requires development of individually modified histone subunits (e.g., NCL, Amber suppression, etc.), followed by in vitro octamer assembly. However, these methods of nucleosome manufacturing are incredibly time-consuming and expensive, due to the fact that each histone subunit must be individually produced and subsequently verified by analytical HPLC and high-resolution mass spectrometry. Although these methods are ideal for large milligram-scale syntheses, they are not appropriate for rapid development of emerging nucleosome targets or large diversity panels for discovery-based applications. Thus, new methods are warranted that will lower costs and accelerate experimental timelines, while still providing reliable performance in downstream assays.

To address these outstanding needs, a novel enzymatic method for accelerated modified recombinant nucleosome manufacturing was established. One embodiment of this approach leverages the *S. aureus*-derived Sortase A transpeptidase to ligate modified histone H3 tails onto nucleosomes assembled with "tailless" H3 histones (FIG. 1A). H3 peptides are engineered to contain the sortase target motif LPATG (SEQ ID NO:14) at their C-terminus, which enables ligation by a sortase allele to an N-terminal GG on the core histone H3 (FIG. 1A). The versatility of this method comes from the modular nature of the tailless nucleosome precursor (tNuc): with one tNuc substrate, it is possible to create a diverse library of H3-modified nucleosomes. H3K9me3 nucleosomes have been produced using Cy2-tagged histone peptides, which allowed one to visualize and accurately quantify ligation efficiency. The resulting nucleosomes (referred to as 'Enzyme' nucleosomes in Figures) had no detectable free DNA (FIG. 1B, top panel), and displayed equal stoichiometric ratios of histones (FIG. 1C, top panel), similar to H3K9me3 nucleosomes prepared by NCL. Analysis of Cy2 fluorescence and immunoblot for H3K9me3 demonstrated that modified H3K9me3 peptide was successfully incorporated into the assembled modified nucleosome (FIGS. 1B-1C). Immunoblot for the unmodified C-terminus of histone H3 revealed a ligation efficiency of ~85% (FIG. 1C, bottom panel), which was consistent across a variety of H3 peptides. This technology delivers a powerful advance in the field, as it enables cost-effective, multiplexed development of single and combinatorially-modified nucleosomes in scalable batches (25-250 µg).

Example 2: Nucleosome Substrates Generated Enzymatically or by NCL Perform Similarly in a Variety of Nucleosome Reader, Writer and Eraser Assays Standard NCL-manufacturing methods produce a "scarless" recombinant nucleosome, meaning that the underlying protein sequence is unaltered by this approach. Thus, it is imperative to functionally validate the present enzymatically modified nucleosomes compared to NCL-derived nucleosomes, as the present method results in an alanine to leucine substitution near the ligation site on histone H3 (A29L in the initial iteration). Here, the performance of NCL- and enzymatically-generated recombinant nucleosomes was compared in nucleosome reader, writer, and eraser assays, using the AlphaScreen™ platform. These assays pair biotinylated nucleosomes with Donor beads, and interacting proteins with appropriate Acceptor beads. Binding of proteins to nucleosomes brings Acceptor and Donor beads into close proximity, resulting in signal proportional to the amount of protein-nucleosome interaction.

For the nucleosome reader assay, the chromodomain of HP1β was incubated with varying concentrations of unmodified or H3K9me3 nucleosomes (generated by recombinant expression (WT), NCL, or enzymatic procedures). As shown in FIG. 2A, the HP1β chromodomain displayed equivalent binding to each H3K9me3 nucleosome, and had no reactivity to unmodified controls. Next, experiments were performed using enzymes that target the H3K9 residue, revealing similar enzymatic activity on both NCL- and enzymatically-prepared nucleosome substrates (FIGS. 2B, 2C). For the eraser assay, H3K9me3 nucleosomes were treated with the lysine demethylase KDM4A, followed by detection using an anti-H3K9me1 antibody (FIG. 2B). The writer assays employed unmodified nucleosomes incubated with the histone methyltransferase G9a, with subsequent detection using an anti-H3K9me2 antibody (FIG. 2C). These studies illustrate the broad utility of enzymatic nucleosome substrates across a wide array of protein binding assays, and confirm their function relative to highly pure NCL-derived nucleosomes.

Example 3: Enzymatically-Derived Nucleosomes are Reliable Substrates for Profiling Antibodies to Specific Histone Post-Translational Modifications One of the main applications of recombinant nucleosome technology is profiling the specificity of antibodies to histone post-translational modifications. Here, the capabilities of NCL- and enzymatically-manufactured nucleosomes were compared as controls for antibody screening experiments on the AlphaScreen™ platform. Three sets of nucleosomes were assembled using each approach: 1) nucleosomes with a modification near the alanine substitution site in the enzymatic approach (H3K27me3); 2) nucleosomes modified at the N-terminus of the histone H3 tail (H3K9me3); and 3) unmodified nucleosomes. Three antibodies were tested per modification. For these assays, nucleosomes were wrapped with biotinylated DNA, and coupled to streptavidin-coated Donor beads, and antibodies were bound to Protein A Acceptor beads. Binding of antibodies to modified nucleosomes brought Acceptor and Donor beads into close proximity, resulting in signal proportional to the amount of antibody-nucleosome interaction. Slightly reduced signal was observed for enzymatic-derived H3K27me3 nucleosome compared to NCL-H3K27me3 (FIGS. 3B, 3D, 3F), most likely due to the neighboring alanine-to-leucine substitution. However, no differences were observed in the detection of H3K9me3 using any of the H3K9me3-specific antibodies (FIGS. 3A, 3C, 3E). Thus, enzymatically-developed recombinant nucleosomes are a reliable substrate for profiling of antibodies to histone post-translational modifications.

Example 4: Enzyme-Mediated Peptide Ligation Enables Unprecedented Access to Combinatorial Histone Post-Translational Modifications The impact of co-occurring, or combinatorial, histone post-translational modifications on chromatin binding proteins is a growing concern in the field. Examining these proteins in the nucleosome context is essential to understanding their physiological activity. Here, the present sortase-derived enzymatic manufacturing method was leveraged to create a set of combinatorial- and single-modified nucleosomes, and the effects of co-occurring H3S10ph on the binding of the HP1β chromodomain and the ATRX ADD domain to H3K9me3 was studied. In these AlphaScreen™ experiments, biotinylated nucleosomes were paired to streptavidin-coated Donor beads, and the HP1β/ATRX domains were coupled to glutathione-coated Acceptor beads. Interaction of proteins with nucleosomes brought Acceptor and Donor beads into close proximity, resulting in increased signal proportional to the amount of protein-nucleosome binding. In each experiment, unmodified and H3S10ph nucleosomes were included as negative controls. The HP1β chromodomain displayed strong specificity for H3K9me3, with no binding to co-modified H3K9me3/

Figure 4A:
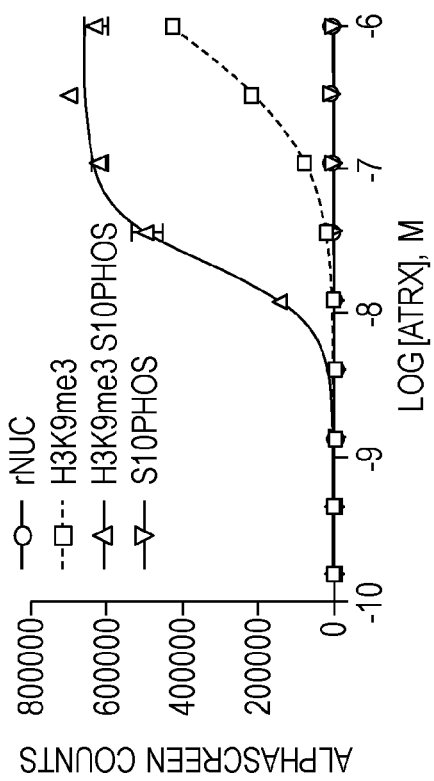
FIGS. 4A-4D show enzyme-mediated peptide ligation enables unprecedented access to combinatorial histone post-translational modifications. Here, the AlphaScreen™ platform was utilized for interrogating chromatin reader domain binding to single- and combinatorially-modified nucleosomes. All nucleosomes were assembled with biotinylated DNA, allowing their capture with streptavidin-coated Donor beads. Protein-nucleosome interactions were quantified using glutathione Acceptor beads and an EnVision® plate reader. (A, B) Titration of the GST-fused HP1α chromodomain (A) and the GST-fused ATRX ADD domain (B) with H3K9me3 and H3K9me3/H3S10ph nucleosomes (Kunowska et al., *Nucleic Acids Res.* 43(3):1418 (2015)). H3S10ph and unmodified nucleosomes were included as negative controls. (C) HP1β binding was quantified at the KdApp for H3K9me3, revealing the expected strong selectivity for single-modified H3K9me3. (D) ATRX binding was quantified at the KdApp for H3K9me3/H3S10ph.
Figure 4B:
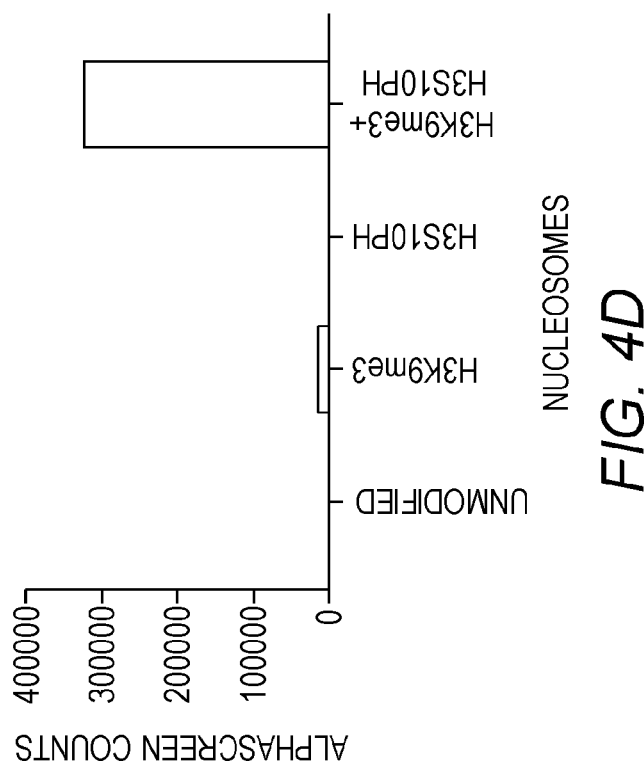
Figure 4C:
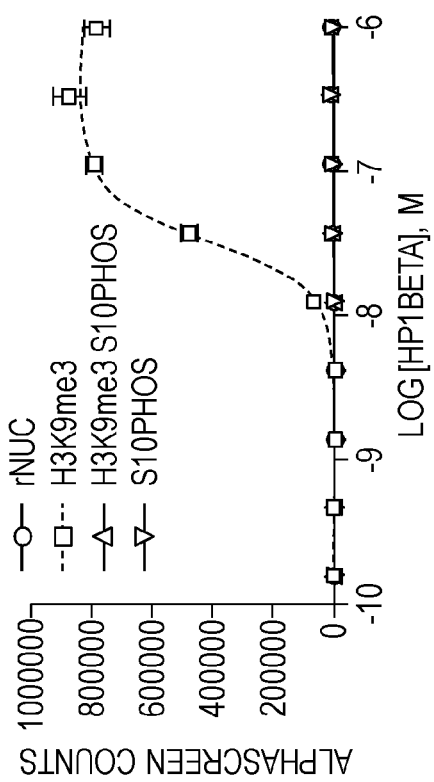
Figure 4D:
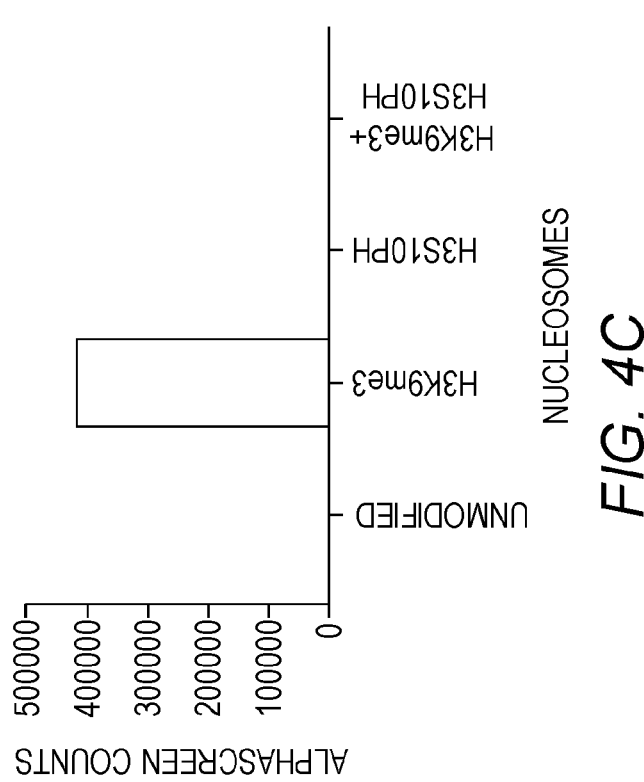

H3S10ph (FIGS. 4A, 4C). In contrast, the ATRX ADD domain displayed increased binding to co-modified H3K9me3/H3S10ph compared to single-modified H3K9me3 (FIGS. 4B, 4D). This work demonstrates that unique combinations of PTMs can both enhance and repress nucleosome reader binding, and provide strong evidence for the importance of developing combinatorial nucleosome substrates.

The foregoing is illustrative of the present invention, and is not to be construed as limiting thereof. The invention is defined by the following claims, with equivalents of the claims to be included therein.

We claim:

1. A method for ligating a histone peptide onto a fully assembled recombinant nucleosome, the nucleosome comprising core histones and a polynucleotide wrapped around the core histones; the method comprising:
   (a) contacting a histone peptide with a transpeptidase to produce a histone peptide-transpeptidase intermediate, wherein the histone peptide comprises a C-terminal transpeptidase recognition site; and
   (b) contacting the histone peptide-transpeptidase intermediate with a fully assembled recombinant nucleosome comprising a modified core histone protein in which the N-terminal tail has been deleted and an amino acid sequence suitable for transpeptidase mediated ligation is added to the N-terminus under conditions sufficient for ligation of the histone peptide to the modified core histone protein;
   thereby producing a fully assembled recombinant nucleosome with a histone peptide ligated thereto.

2. A fully assembled recombinant nucleosome with a histone peptide ligated thereto, prepared by the method of claim 1.

3. A library of recombinant nucleosomes, prepared by the method of claim 1.

4. A kit comprising the fully assembled recombinant nucleosome of claim 2.

5. A kit comprising the library of recombinant nucleosomes of claim 3.

6. The method of claim 1, wherein the transpeptidase is a sortase family enzyme.

7. The method of claim 6, wherein the sortase is a wild-type sortase enzyme.

8. The method of claim 7, wherein the sortase enzyme is *Staphylococcus aureus* sortase A.

9. The method of claim 6, wherein the sortase enzyme comprises one or more mutated residues that alter activity or specificity.

10. The method of claim 1, wherein the fully assembled nucleosome comprises at least one post-translational modification.

11. The method of claim 10, wherein the at least one post-translational modification is selected from lysine methylation, lysine acylation, serine phosphorylation, lysine ubiquitylation, arginine methylation, and any combination thereof.

12. The method of claim 1, wherein the fully assembled nucleosome comprises at least one histone variant.

13. The method of claim 1, wherein the fully assembled nucleosome comprises at least one post-transcriptional modification on the polynucleotide sequence.

14. The method of claim 13, wherein the at least one modification is selected from 5-methylcytosine, 5-hydroxymethylcytosine, 5,6-dihydrouracil, 7-methylguanosine, xanthosine, inosine, and any combination thereof.

15. The method of claim 1, wherein the modified core histone protein is histone H2A, histone H3, a variant backbone of H3 selected from H3.1, H3.2, or H3.3, or histone H4.

16. The method of claim 1, wherein the transpeptidase recognition site is a sortase family enzyme recognition site.

* * * * *

UNITED STATES PATENT AND TRADEMARK OFFICE
CERTIFICATE OF CORRECTION

PATENT NO. : 11,739,128 B2
APPLICATION NO. : 16/977218
DATED : August 29, 2023
INVENTOR(S) : Cowles et al.

Page 1 of 1

It is certified that error appears in the above-identified patent and that said Letters Patent is hereby corrected as shown below:

On the Title Page

(56) References Cited, OTHER PUBLICATIONS, Column 2, Line 4, NGUYEN, GIANG K.T, et al. cite: Please correct "Site-Specific N-Terminai Labeling" to read --Site-Specific N-Terminal Labeling--

(56) References Cited, OTHER PUBLICATIONS, Column 2, Line 19, HARIDAS, V , et al. cite: Please correct "Sortase-Based Bio-organic Strategies far" to read --Sortase-Based Bio-organic Strategies for--

In the Specification

Column 4, Line 44: Please correct "113," to read --H3,--

Column 5, Line 31: Please correct "HP10" to read --HP1β--

Column 5, Line 36: Please correct "HP113" to read --HP1β--

Column 19, Line 58: Please correct "HP113" to read --HP1β--

Signed and Sealed this
Thirty-first Day of October, 2023

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 130
<212> TYPE: PRT
<213> ORGANISM: Homo sapiens

<400> SEQUENCE: 1

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 2
<211> LENGTH: 126
<212> TYPE: PRT
<213> ORGANISM: Homo sapiens

<400> SEQUENCE: 2

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Ser Arg Lys Glu Ser Tyr Ser Val Tyr Val Tyr Lys Val Leu Lys Gln
            35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 3
<211> LENGTH: 136
<212> TYPE: PRT
<213> ORGANISM: Homo sapiens

<400> SEQUENCE: 3

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 4
<211> LENGTH: 136
<212> TYPE: PRT
<213> ORGANISM: Homo sapiens

<400> SEQUENCE: 4

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 5
<211> LENGTH: 103
<212> TYPE: PRT
<213> ORGANISM: Homo sapiens

```
<400> SEQUENCE: 5

Met Ser Gly Arg Gly Lys Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
        50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 6
<211> LENGTH: 5
<212> TYPE: PRT
<213> ORGANISM: Artificial
<220> FEATURE:
<223> OTHER INFORMATION: recognition site
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 6

Leu Pro Xaa Thr Gly
1               5

<210> SEQ ID NO 7
<211> LENGTH: 5
<212> TYPE: PRT
<213> ORGANISM: Artificial
<220> FEATURE:
<223> OTHER INFORMATION: recognition site

<400> SEQUENCE: 7

Asn Pro Gln Thr Asn
1               5

<210> SEQ ID NO 8
<211> LENGTH: 6
<212> TYPE: PRT
<213> ORGANISM: Artificial
<220> FEATURE:
<223> OTHER INFORMATION: recognition site
<220> FEATURE:
<221> NAME/KEY: MISC_FEATURE
<222> LOCATION: (3)..(3)
<223> OTHER INFORMATION: Xaa is Q or K
<220> FEATURE:
<221> NAME/KEY: MISC_FEATURE
<222> LOCATION: (4)..(4)
<223> OTHER INFORMATION: Xaa is T or S
<220> FEATURE:
<221> NAME/KEY: MISC_FEATURE
<222> LOCATION: (5)..(5)
<223> OTHER INFORMATION: Xaa is N, G or S
<220> FEATURE:
<221> NAME/KEY: MISC_FEATURE
<222> LOCATION: (6)..(6)
<223> OTHER INFORMATION: Xaa is D or A
```

```
<400> SEQUENCE: 8

Asn Pro Xaa Xaa Xaa Xaa
1               5

<210> SEQ ID NO 9
<211> LENGTH: 5
<212> TYPE: PRT
<213> ORGANISM: Artificial
<220> FEATURE:
<223> OTHER INFORMATION: recognition site

<400> SEQUENCE: 9

Leu Pro Leu Thr Gly
1               5

<210> SEQ ID NO 10
<211> LENGTH: 10
<212> TYPE: PRT
<213> ORGANISM: Artificial
<220> FEATURE:
<223> OTHER INFORMATION: recognition site
<220> FEATURE:
<221> NAME/KEY: MISC_FEATURE
<222> LOCATION: (2)..(4)
<223> OTHER INFORMATION: Xaa is any naturally occurring amino acid
<220> FEATURE:
<221> NAME/KEY: MISC_FEATURE
<222> LOCATION: (6)..(7)
<223> OTHER INFORMATION: Xaa is any naturally occurring amino acid

<400> SEQUENCE: 10

Trp Xaa Xaa Xaa Val Xaa Xaa Tyr Pro Lys
1               5                   10

<210> SEQ ID NO 11
<211> LENGTH: 5
<212> TYPE: PRT
<213> ORGANISM: Artificial
<220> FEATURE:
<223> OTHER INFORMATION: recognition site

<400> SEQUENCE: 11

Leu Pro Asn Thr Ala
1               5

<210> SEQ ID NO 12
<211> LENGTH: 5
<212> TYPE: PRT
<213> ORGANISM: Artificial
<220> FEATURE:
<223> OTHER INFORMATION: recognition site
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 12

Leu Ala Xaa Thr Gly
1               5

<210> SEQ ID NO 13
<211> LENGTH: 5
<212> TYPE: PRT
<213> ORGANISM: Artificial
<220> FEATURE:
<223> OTHER INFORMATION: recognition site
```

```
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 13

Ala Pro Xaa Thr Gly
1               5

<210> SEQ ID NO 14
<211> LENGTH: 5
<212> TYPE: PRT
<213> ORGANISM: Artificial
<220> FEATURE:
<223> OTHER INFORMATION: recognition site

<400> SEQUENCE: 14

Leu Pro Ala Thr Gly
1               5
```